US00PP29894P3

(12) United States Plant Patent
Probasco et al.

(10) Patent No.: US PP29,894 P3
(45) Date of Patent: Nov. 27, 2018

(54) HOP PLANT NAMED 'HBC 522'

(50) Latin Name: *Humulus lupulus*
Varietal Denomination: HBC 522

(71) Applicants: Eugene G. Probasco, Yakima, WA (US); Jason Perrault, Toppenish, WA (US)

(72) Inventors: Eugene G. Probasco, Yakima, WA (US); Jason Perrault, Toppenish, WA (US)

(73) Assignee: Hop Breeding Company, L.L.C., Yakima, WA (US)

( * ) Notice: Subject to any disclaimer, the term of this patent is extended or adjusted under 35 U.S.C. 154(b) by 0 days.

(21) Appl. No.: 15/330,749

(22) Filed: Nov. 1, 2016

(65) Prior Publication Data

US 2017/0127590 P1 May 4, 2017

Related U.S. Application Data

(60) Provisional application No. 62/285,569, filed on Nov. 2, 2015.

(51) Int. Cl.
*A01H 5/00* (2018.01)

(52) U.S. Cl.
USPC ..... Plt./236
CPC ..... *A01H 5/00* (2013.01)

(58) Field of Classification Search
USPC ..... Plt./236
CPC ..... A01H 5/00
See application file for complete search history.

*Primary Examiner* — Kent L Bell
(74) *Attorney, Agent, or Firm* — Svendsen Legal, LLC

(57) ABSTRACT

A new hop plant named 'HBC 522' is disclosed. 'HBC 522' is used for its exceptional and unique aromatic qualities.

6 Drawing Sheets

Genus and species: *Humulus lupulus*.
Variety denomination: 'HBC 522'.

STATEMENT REGARDING FEDERALLY SPONSORED RESEARCH OR DEVELOPMENT

None

BACKGROUND OF THE INVENTION

'HBC 522' is a product of a controlled breeding program carried out by the inventors in the Yakima Valley of Washington State. 'HBC 522' was one of several seedlings resulting from a controlled cross made in 2006 with female parent 'Columbus' (U.S. Plant Pat. No. 10,956) and male parent '986-2' (unpatented). A single plant of 'HBC 522' was selected in 2009, and in 2010 the plant was asexually reproduced via softwood cuttings in a greenhouse near Toppenish, Wash., and expanded to 30 plants, which were planted in the area of Toppenish, Wash. The plants were observed and evaluated for several years, and in 2014 a 1 acre test plot of 'HBC 522' was established in the area of Moxee, Wash. Throughout several generations of asexual propagation, 'HBC 522' has been observed to retain its distinctive characteristics and remain true to type.

COMPARISON OF 'HBC 520' TO PARENT PLANT AND COMARISON CULTIVAR

'HBC 522' is distinguishable from its male parent '986-2' with flowers that develop into mature hop cones without producing pollen, while flowers of '986-2' produce pollen without developing into mature hop cones.

Table 1. below, sets forth some of the distinguishing characteristics of 'HBC 522' as compared to its female parent 'Columbus', and to the 'Cascade' cultivar as a closely comparable cultivar.

TABLE 1

| | INSTANT CV. 'HBC 522' | PARENT 'COLUMBUS' | COMPARISON CV. 'CASCADE' |
|---|---|---|---|
| Alpha (% of cone weight) | 9.9-11.7 | 14.5-17.5 | 5.5-9.0 |
| Beta (% of cone weight) | 4.5-5.4 | 4.5-6.0 | 6.0-7.5 |
| Co-humulone (% of alpha acids) | 24.8 | 28-30 | 30-35 |
| Total Oil (mL/100 g) | 1.4-2.3 | 2.5-4.5 | 0.8-0.25 |
| Myrcene (% of total oil) | 36.95 | 45-55 | 45-60 |
| Linalool (% of total oil) | 0.64 | 0.4-0.6 | 0.3-0.6 |
| Caryophyllene (% of total oil) | 8.44 | 6-10 | 5-9 |
| Farnesene (% of total oil) | 0.52 | <1.0 | 6-9 |
| Humulene (% of total oil) | 13.18 | 9-14 | 14-20 |
| Aroma Profile | citrus, floral | earthy, citrus, spicy | citrus, floral |

BRIEF DESCRIPTION OF THE PHOTOGRAPHS

Figure 1:
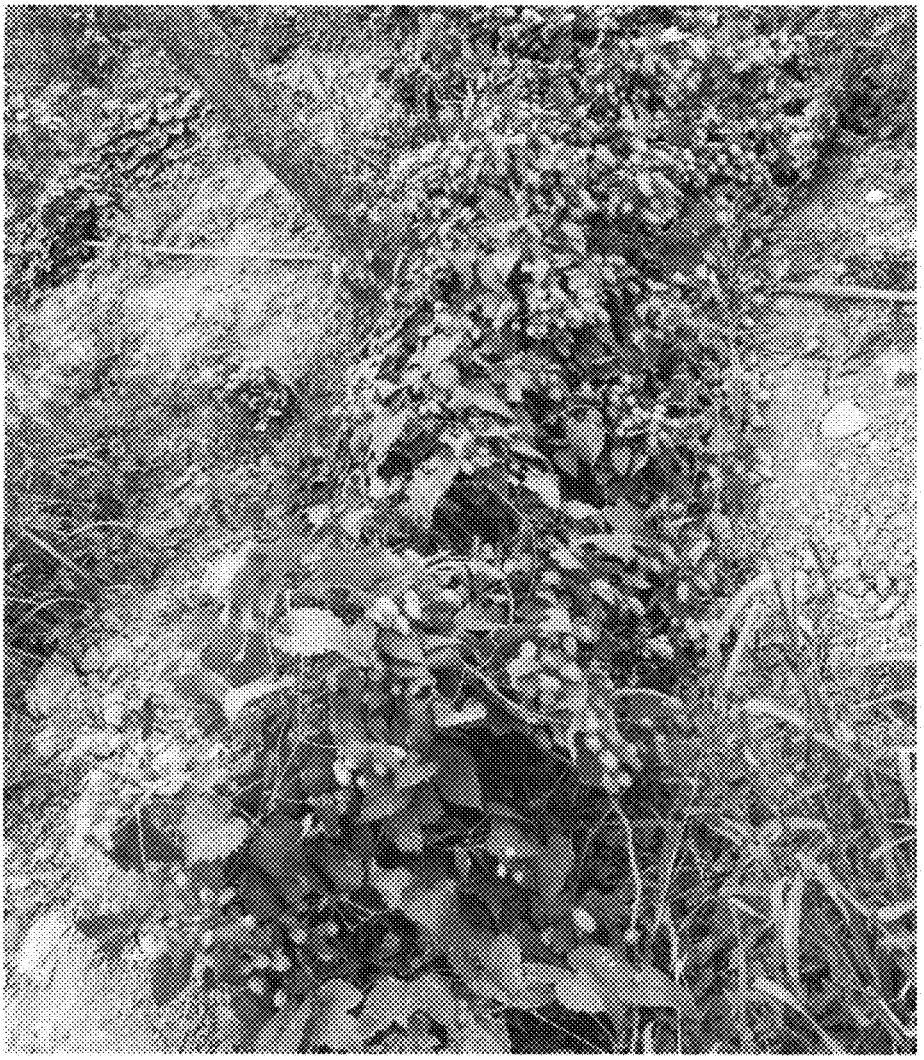
FIG. 1 illustrates a mature 'HBC 522' hop plant grown on a trellis.
Figure 2:
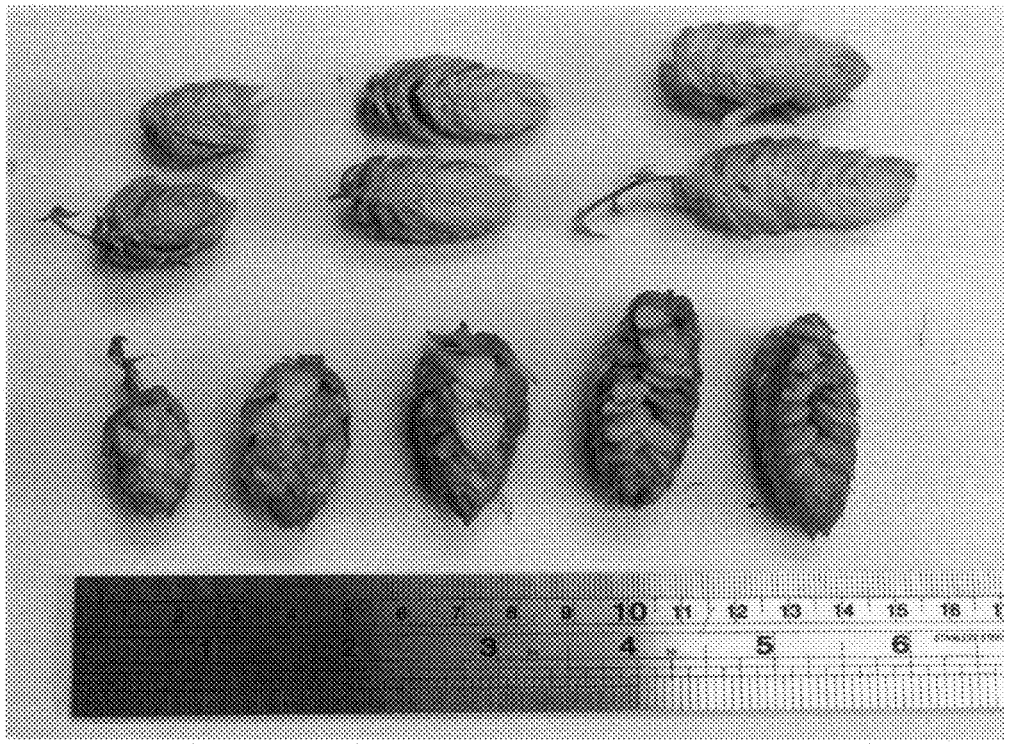
FIG. 2 illustrates whole cones and cross sections of cones of the 'HBC 522' hop plant.
Figure 3:
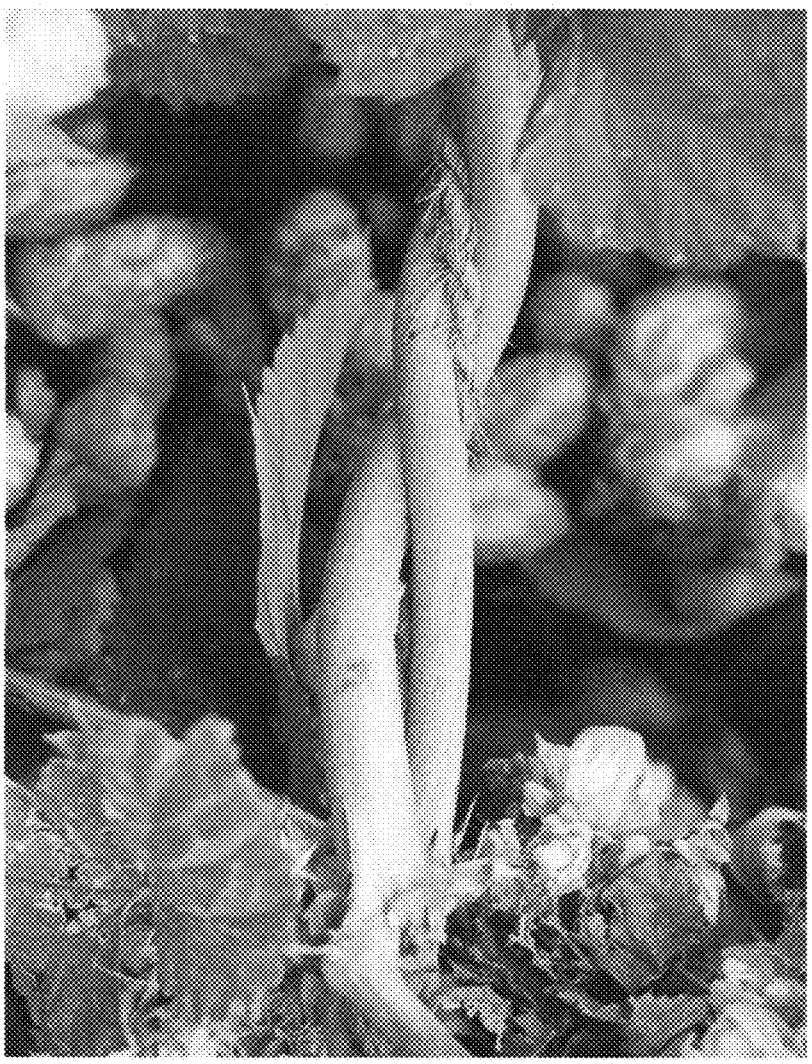
FIG. 3 illustrates the bine of a mature 'HBC 522' hop plant.
Figure 4:
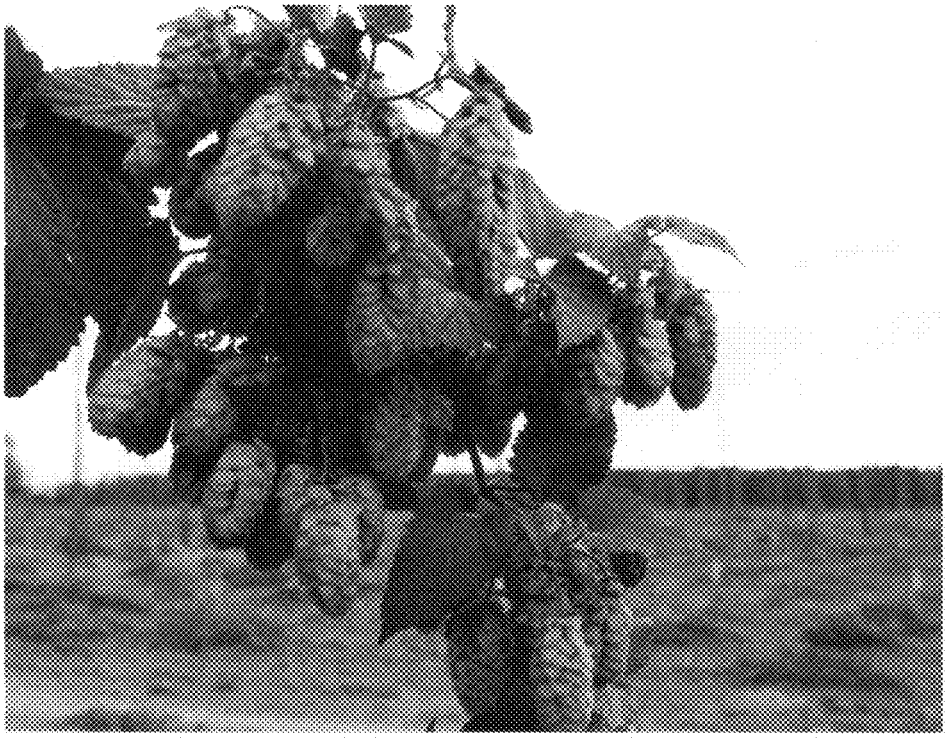
FIG. 4 illustrates cones on a mature 'HBC 522' hop plant.
Figure 5:
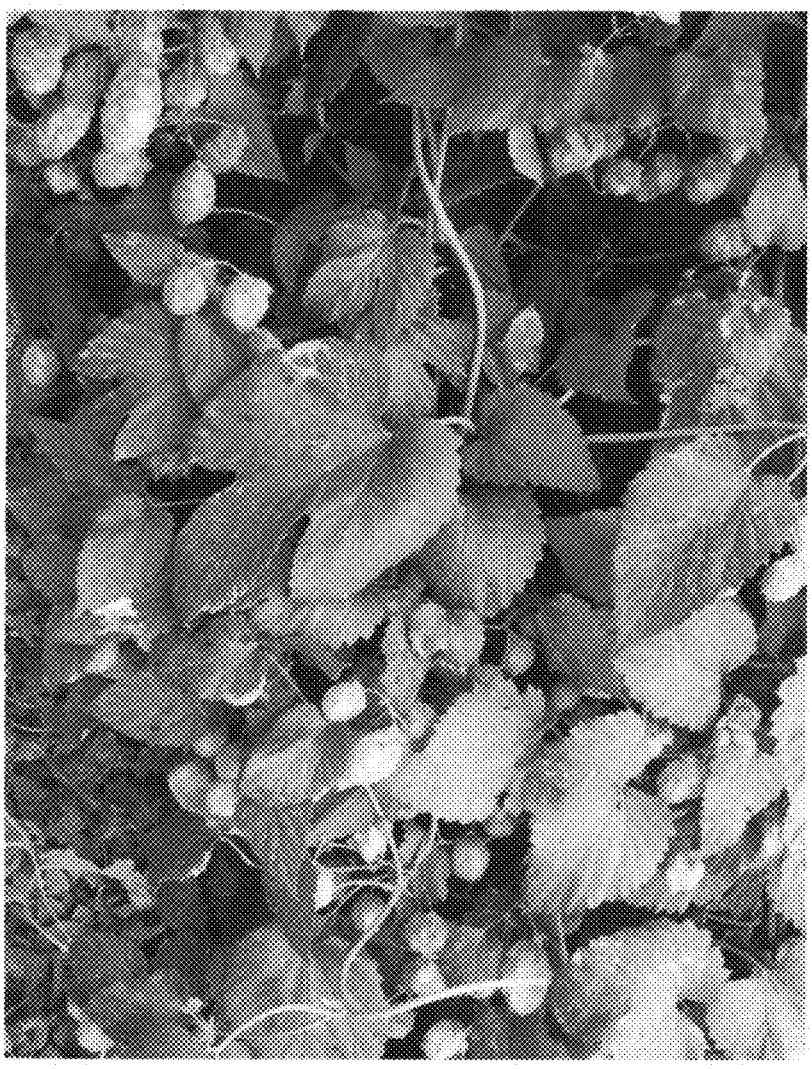
FIG. 5 illustrates leaves on a mature 'HBC 522' hop plant.
Figure 6:
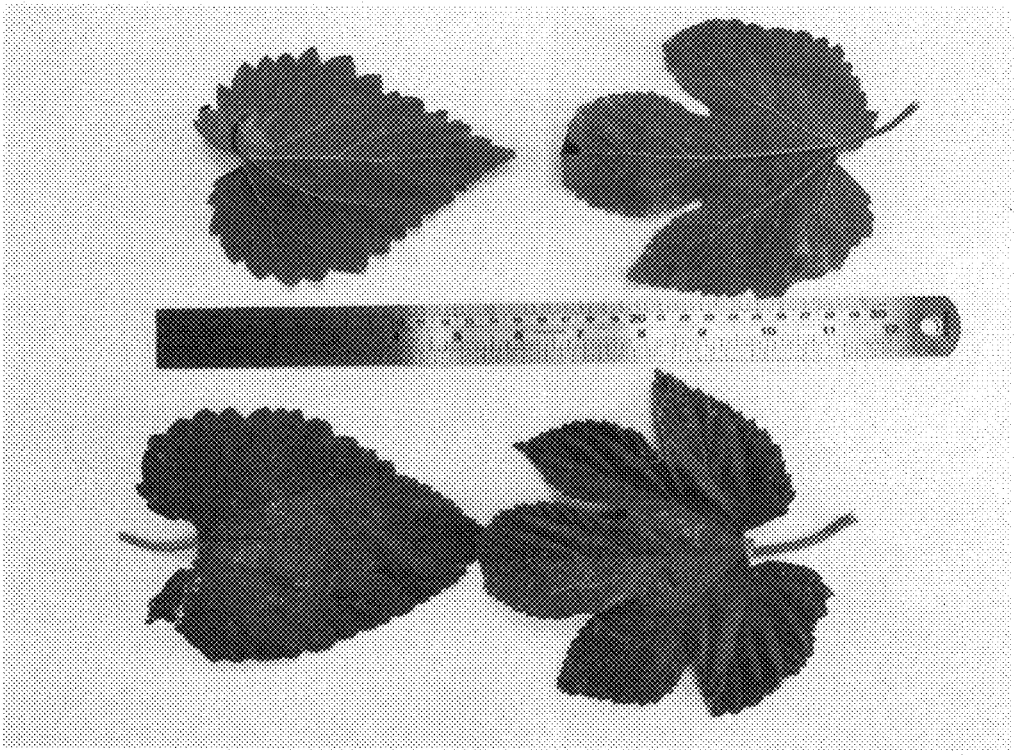
FIG. 6 illustrates leaves of the 'HBC 522' hop plant.

The colors of these illustrations may vary with lighting conditions and, therefore, color characteristics of this new variety should be determined with reference to the observations described herein, rather than from these illustrations alone.

DETAILED BOTANICAL DESCRIPTION

The following description is based on observations made during the 2009-2015 growing seasons at Toppenish, Wash. It should be understood that the characteristics described will vary somewhat depending upon cultural practices and climatic conditions, and can vary with location and season. Quantified measurements are expressed as an average of measurements taken from a number of individual plants of the new variety. The measurements of any individual plant or any group of plants, of the new variety may vary from the stated average. All color references are based on The Royal Horticultural Society Colour Chart.

Ploidy: Diploid (2n=2x).

Sex: Female.

Disease/pest resistance/susceptibility: Resistant to powdery mildew. Reaction to other common hop diseases unknown, none observed to date.

Use: Brewing beer and ale.

Harvest date: September (during 2009 to 2015 growing seasons at Toppenish, Wash.).

Crop yield: Approximately between 2,000 lbs per acre and 2,400 lbs per acre.

Plant shape: Climbing bine, columnar growth.

Quality characteristics (Averages):

*Alpha acid* (*as % of cone weight*).—9.9% to 11.7%.
*Beta acid* (*as % of cone weight*).—4.5% to 5.4%.
*Cohumulone* (*as % of alpha acids*).—24.8%.
*Total oil* (*ml*/100 *g of cones*).—1.4 ml to 2.3 ml.
*Storageability* (*% loss*).—11% to 13%.

Oil analytical characteristics (Averages):

*A-pinene*.—0.04% Total Oil.
*B-pinene*.—0.90% Total Oil.
*Myrcene*.—36.95% Total Oil.
2-*methyl-butyl isobutyrate*.—0.09% Total Oil.
*Limonene*.—0.12% Total Oil.
*Linalool*.—0.64% Total Oil.
*Caryophyllene*.—8.44% Total Oil.
*Farnesene*.—0.52% Total Oil.
*Humulene*.—13.18% Total Oil.
*Citral*.—1.12% Total Oil.
*Geranyl acetate*.—0.16% Total Oil.
*Citronellol*.—3.36% Total Oil.
*Nerol*.—0.39% Total Oil.
*Geraniol*.—0.05% Total Oil.
*B-lonene*.—0.03% Total Oil.

Bine:

*Color*.—Yellow-Green 143B.
*Stripe present*.—Yes.
*Stripe color*.—Red 42B.
*Stipule direction*.—Horizontal.
*Stipule color*.—Yellow-Green N144A.
*Average number of stipule per bine*.—Two per node.
*Typical and observed bine length*.—Typical bine growth of 20 feet to 24 feet, when grown on a standard eighteen foot trellis.
*Internode length of bine*.—16 cm to 23 cm.
*Bine diameter*.—11 mm at base; 10 mm at nine feet; 9 mm at terminal end of eighteen feet.

Lateral:

*Color*.—Green 143B.
*Typical and observed lateral length*.—99 cm to 160 cm.
*Internode length of laterals*.—15 cm to 21.5 cm.
*Lateral diameter*.—4 mm to 5 mm at the base; and 0.5 mm to 1 mm at the terminal end.

Leaf:

*Arrangement*.—Opposite.
*Shape*.—Palmate.
*Leaf apex descriptor*.—Acuminate.
*Leaf base descriptor*.—Cordate.
*Average length of mature leaf*.—13 cm.
*Average width of mature leaf*.—11.5 cm.
*Color of mature leaf upper surface*.—Green 136A.
*Color of mature leaf lower surface*.—Green 137B.
*Color of immature leaf upper surface*.—Green 131A.
*Color of immature leaf lower surface*.—Green 132B.
*Number of lobes*.—1 to 3.
*Margin*.—Serrate.
*Serrations per inch*.—3.
*Average petiole length* (*mature*).—50 mm.
*Petiole diameter*.—4 mm to 5 mm.
*Petiole color*.—Yellow-Green 144B.
*Petiole color at base*.—Yellow-Green 144B.
*Venation*.—Palmate.
*Vein color*.—Green 138A.

Cone:

*Avg. length*.—34 mm.
*Avg. diameter*.—20 mm.
*Avg. weight*.—800 mg to 1000 mg.
*Pickability*.—Good.
*Bract tip color*.—Green 141A.
*Bract inner surface color*.—Green 141A.
*Bract outer surface color*.—Green 142A.
*Bract base color*.—Green 142A.
*Bract margin*.—Entire.
*Bract base*.—Rounded.
*Bracteole color* (*both surfaces*).—Yellow-Green 150C.
*Bracteole typical length*.—12 mm to 18 mm.
*Bracteole typical width*.—8 mm to 10 mm.
*Cone shape*.—Oblong.
*Bract shape*.—Orbicular.
*Bract tip shape*.—Cuspidate.
*Bracteole shape*.—Ovate.

What is claimed:

1. A new and distinct Hop plant as illustrated and described herein.

* * * * *